(12) United States Patent
Recine et al.

(10) Patent No.: US 9,393,183 B2
(45) Date of Patent: Jul. 19, 2016

(54) THREE-LAYERED HAIR CONDITIONING COMPOSITION AND CONSUMER PRODUCT

(71) Applicants: Jennifer Marie Recine, Farmingdale, NY (US); John J. Salto, Deer Park, NY (US); Geoffrey Hawkins, Yardley, PA (US)

(72) Inventors: Jennifer Marie Recine, Farmingdale, NY (US); John J. Salto, Deer Park, NY (US); Geoffrey Hawkins, Yardley, PA (US)

(73) Assignee: ELC MANAGEMENT, Melville, NY (US)

(*) Notice: Subject to any disclaimer, the term of this patent is extended or adjusted under 35 U.S.C. 154(b) by 186 days.

(21) Appl. No.: 13/948,920

(22) Filed: Jul. 23, 2013

(65) Prior Publication Data

US 2014/0199353 A1 Jul. 17, 2014

Related U.S. Application Data

(60) Provisional application No. 61/675,377, filed on Jul. 25, 2012.

(51) Int. Cl.
| | | |
|---|---|---|
| A61Q 17/04 | (2006.01) | |
| A61Q 19/00 | (2006.01) | |
| A61K 8/02 | (2006.01) | |
| A61K 45/06 | (2006.01) | |
| A61K 9/70 | (2006.01) | |
| A61K 8/03 | (2006.01) | |
| A61Q 5/00 | (2006.01) | |
| A61K 8/34 | (2006.01) | |
| A61K 8/891 | (2006.01) | |
| A61K 8/92 | (2006.01) | |

(52) U.S. Cl.
CPC . *A61K 8/03* (2013.01); *A61K 8/345* (2013.01); *A61K 8/891* (2013.01); *A61K 8/922* (2013.01); *A61Q 5/00* (2013.01); *A61K 2800/30* (2013.01); *A61K 2800/31* (2013.01); *A61K 2800/33* (2013.01)

(58) Field of Classification Search
CPC ... A61K 2300/00; A61K 47/10; A61K 9/209; A61K 2800/33; A61K 2800/10; A61K 9/0014; A61Q 19/00
USPC ............................ 424/443, 400, 401, 59, 472
See application file for complete search history.

(56) References Cited

U.S. PATENT DOCUMENTS

| | | | | |
|---|---|---|---|---|
| 4,126,220 | A * | 11/1978 | Roccaforte | 206/782 |
| 7,988,981 | B2 | 8/2011 | Di Puccio Pagano | |
| 2004/0018163 | A1* | 1/2004 | Yu | 424/70.12 |
| 2004/0096404 | A1* | 5/2004 | Zofchak et al. | 424/59 |
| 2005/0249758 | A1* | 11/2005 | Di Puccio Pagano | 424/401 |
| 2007/0086962 | A1* | 4/2007 | Bandyopadhyay et al. | 424/59 |
| 2007/0128141 | A1* | 6/2007 | Myers | 424/70.1 |
| 2007/0135319 | A1* | 6/2007 | Wei et al. | 510/101 |
| 2011/0152384 | A1* | 6/2011 | Gunn et al. | 514/784 |

FOREIGN PATENT DOCUMENTS

KR     10-2009-0004050 A     1/2009

OTHER PUBLICATIONS

New Jersey Department of Health and Senior Services. Hazardous Substance Fact Sheet—Mineral Oil. Jun. 2001. p. 1.*
Premier Specialties. New Products & Technology—*Elaeis oleifera* (Palm) Oil. May 8, 2010. p. 3.*
Bird, Stephanie Rose. The big book of SOUL—Kalahari Seed Oil. 2010. p. 3.*
Beauty Pose. Glam Glossary: Ximenia Americana Oil. Sep. 25, 2010. p. 1.*
Gwang-Ho et al. Translation of KR 10-2009-0004050. Jan. 12, 2009. pp. 1-13.*

* cited by examiner

*Primary Examiner* — Frederick Krass
*Assistant Examiner* — Tracy Liu
(74) *Attorney, Agent, or Firm* — Peter Giancana

(57) ABSTRACT

Personal care compositions comprising three liquid layers, particular useful for treating hair. The compositions are visually three separate layers. One layer comprises an oil phase, one layer comprises a polyol phase, and one layer comprises a silicone phase. The compositions can be mixed homogenously upon shaking, and remain homogenous for a sufficient period of time to allow the consumer to use the product, before it separates into three distinct layers again. The compositions do not have substantial amounts of surfactants or emulsifiers, and no more than 1% of salts or mineral oil.

20 Claims, No Drawings

THREE-LAYERED HAIR CONDITIONING COMPOSITION AND CONSUMER PRODUCT

CROSS-REFERENCE TO RELATED APPLICATIONS

This application claims priority from Provisional U.S. patent application Ser. No. 61/675,377 filed Jul. 25, 2012.

FIELD OF THE INVENTION

The present invention relates to personal care compositions comprising three liquid layers. In particular, such compositions are particularly useful for treating hair.

BACKGROUND

Dual layered or multi-layered cosmetic compositions have become popular over the years, because of their appealing appearance. Such compositions have been developed for applications in skin care and hair care. Multi-layered liquid products in other fields are also known. In some multi-layered products, one liquid layer is incompatible with one or more other liquid layers. By "incompatible", we mean that the layers are mutually insoluble and mutually non-reactive. Because of this, the less dense layers tend to sit on top of the more dense layers. We consider such a product "stable" if the layer separation can be maintained for a defined period of time, and if the interface between two layers is no thicker than a specified thickness. The separated layers may be mixed within each other prior to use, by shaking the composition. Depending on the composition, a typical consumer product may take several seconds or several minutes of shaking to form a homogenous mixture of the layers. In part, it depends on the viscosity of the layers, and the size and shape of the container. After shaking, in order to maintain the mixed state temporarily, (i.e. during consumer use), some products use surfactant. But if too much surfactant is used, the layers will take too long to separate.

Other multi-layered products may use certain agents that are able to maintain separation of two or more layers that might otherwise mix. For example, some existing multi-layered (two or more layers) cosmetic compositions use emulsifiers and/or salts to achieve and/or maintain a stable multi-layered system. However, emulsifiers, surfactants, and salts can be irritating or harmful to the user if their concentration is too high. For example, U.S. Pat. No. 7,988,981 teaches 8-18% of water soluble salts as a necessary component of a multi-layered cosmetic composition. This is unlike the present invention which has no more than about 1% salt content, and typically much less. '981 implies that such a low concentration of salt would be insufficient to achieve layer separation (see column 2, lines 57-63). Nevertheless, the present invention achieves clean layer separation, even by going against the teaching of '981. The '981 patent also claims compositions having mineral oil. However, some consumers have developed a negative perception of mineral oils in cosmetics. In contrast, the present invention may comprise no more than about 1% mineral oil.

Furthermore, with repeated mixing of a composition during regular use, some existing multi-layered systems can take longer and longer to return to a stable, separated state, and the product becomes less appealing over time. This is unlike the present invention.

Natural oils have been used for centuries to condition human hair, but when used alone, they can impart a stickiness that is undesirable and unappealing to the user. Silicones have been used in hair care to provide a silky and smooth feel, but can leave an unnatural shine behind. To mitigate these problems, hydrophilic ingredients may be used. In that case, emulsifiers have often been used to combine oils, silicones and hydrophilic materials into an emulsion. However, emulsions do not have the appeal of well executed multi-layered compositions. As such, there is a need for stable, multi-layered compositions comprising natural oils, silicones, and hydrophilic ingredients without substantial amounts of surfactants and emulsifiers. Furthermore, it is desirable to incorporate into a multi-layered composition, ingredients that are beneficial to hair care, such as novel combinations of certain essential oils and various hydrophilic ingredients.

SUMMARY

Compositions of the present invention are visually three separate layers. One layer comprises an oil phase, one layer comprises a polyol phase, and one layer comprises a silicone phase. The compositions can be mixed homogenously upon shaking, and remain homogenous for a sufficient period of time to allow the consumer to use the product, before it separates into three distinct layers again. The present invention addresses the above mentioned issues without using substantial amounts of surfactants or emulsifiers, no more than 1% of salts or mineral oil. The present invention may be manifested in various types of cosmetic, personal care or pharmaceutical formulations. Particularly suitable are compositions for the treatment of keratin fibers, especially of hair.

"Comprise" means that an element or group of elements may not be limited to those explicitly recited, but may include additional unrecited elements. Reference to liquid ingredients means that the ingredients are liquid at temperatures and pressures of normal consumer use.

DETAILED DESCRIPTION

Compositions of the present invention comprise three layers, top, middle and bottom. In general, the top layer is the least dense of the three layers, and the bottom layer is the most dense. The top and middle layers are separated by an interface and the middle and bottom layers are separated by an interface.

Top Layer

Based on total weight of the composition, the top layer is present in a range of from 10% to 40%, more preferably from or 10% to 30% or 20% to 40% and even more preferably 20%-30%. In preferred embodiments of the invention, the top layer of the composition comprises a liquid oil phase. The liquid oil phase comprises one or more base oils. The one or more base oils make up at least 50% of the top layer, preferably at least 60%, more preferably at least 70%, and most preferably at least 80% by weight of the top layer. The oils can be selected from plant or synthetic sources, and preferably offer some benefit to the hair (i.e. shine, substantivity, moisturization, cuticle repair, etc.). Some examples of useful base oils include jojoba, sweet almond oil, meadow foam seed oil, olive oil, kukui oil, castor oil, avocado oil, macadamia oil, elaeis oleifera (palm) kernel oil, and apricot kernel oil. Preferably, the composition has no mineral oil. If mineral oil is used it should be no more than 1% of the total composition by weight. In preferred embodiments of the invention, the base oil is jojoba. We have found that of the useful oils, jojoba in excess of 50% of the liquid oil phase gives excellent layer separation with a clean, thin interface, and makes for a very clear top layer.

The liquid oil phase may also comprise one or more liquid oils in addition to the base oil. Also, in preferred embodiments, the liquid oil phase comprises one or more essential oils having one or more hair care benefits. Some examples of useful oils include: palm kernel oil, elaeis oleifera fruit oil, coconut oil, watermelon seed oil, ximenia Americana seed oil, kukui seed oil, sclerocarya birrea seed oil, babassu oil, jojoba oil, commiphora wightii oil and gardenia flower extract. In preferred embodiments of the invention, the liquid oil phase comprises at least one essential oil that is beneficial to hair, but no mineral oil. In more preferred embodiments the liquid oil phase of the top layer comprises palm kernel oil, elaeis oleifera fruit oil, coconut oil, watermelon seed oil, ximenia Americana seed oil, kukui seed oil, and sclerocarya birrea seed oil, but no mineral oil.

Middle Layer

Based on total weight of the composition, the middle layer is present in a range of 20% to 60%, more preferably from 30% to 50%. In preferred embodiments of the invention, the middle layer of the composition comprises a liquid silicone phase. The liquid silicone phase may comprise one or more liquid silicones. The choice of silicones is crucial to the stability and aesthetics of the composition. For example, the silicone phase must be less dense than the polyol phase, but more dense than the oil phase in order for it to remain as the middle layer. Also, if the viscosity of the silicone phase is too low the composition would separate too quickly after shaking If the viscosity is too high, the layers of the composition may fail to separate or separate very slowly. Useful liquid silicones are linear, and have a viscosity ranging from 10cps to 300,000 cps, preferably from 100cps to 100,000 cps. In some preferred embodiments, the viscosity of the middle layer as a whole should be less than about 10,000 cps. In general, branched silicones in appreciable quantities should be avoided, as they add too much viscosity.

Preferably, all of the liquid silicones in the middle layer are clear. One or more of the liquid silicones may also be colorless. Preferably, all of the liquid silicones in the middle layer are colorless. A clear, colorless middle layer gives the finished composition a clean fresh appearance, and provides maximum contrast with shaded top and bottom layers.

Preferably, at least one of the liquid silicones is beneficial to hair. One or more linear dimethicones (polydimethylsiloxanes; approximately 0.965 g/cm$^3$) are most preferred.

Bottom Layer

Based on total weight of the composition, the bottom layer is present in a range of 10% to 40%, more preferably from or 10% to 30% or 20% to 40% and even more preferably 20% - 30%. The bottom layer of the composition comprises a liquid polyol phase. The liquid polyol phase may comprise one or more liquid polyols. In some preferred compositions of the invention the one or more liquid polyols make up at least 50% of the bottom layer by weight. Preferred liquid polyols include diols and triols, such as glycols and glycerine. In some preferred embodiments, butylene glycol, propanediol and glycerin have been found to be useful for holding the three layers in a mixed, homogenous state long enough for the consumer to use the product, but then allowing the layers to break apart within a certain time, when the product is at rest.

The bottom layer may also contain water, water-soluble electrolytes, saccharides, or combinations of both electrolytes and saccharides. The concentration of the water-soluble electrolytes and/or saccharides is important to maintaining the integrity of the phases. If the concentration of the electrolytes or saccharides is too high, the composition can leave an unpleasant residue on the hair. But if the concentration of the electrolytes or saccharides is too low, then the layers might "bleed" into each other, making the interface unacceptably thick, and making the product less stable and less attractive. "Too high" or "too low" may be determined by trial and error.

Layer Densities

As described above, each of the three layers comprise a certain phase (oil, silicone or polyol). With the definition of "comprise" given herein, each layer may have elements which are not considered part of the associated phase. Nevertheless, within each layer, all of the components of the layer must cohere together to form a layer that is uniform and identifiable by an acceptably thin, clean interface. By "cohere" we mean that there should be no unwanted migration of some amount of an ingredient from one layer to another layer. By "acceptably thin interface" we mean that an interface between two layers (top/middle and middle/bottom) is less than 0.5 mm, preferably less than 0.25 mm.

The liquid polyol phase makes up most (more than 50%) of the bottom layer of the composition. The liquid diols and triols typically considered for use in the liquid polyol phase tend to have a density greater than the density of water (1 g/cm$^3$). For example, propanediol is about 1.036 g/cm$^3$; butylene glycol is about 1.0053 g/cm$^3$; and glycerin is about 1.251 g/cm$^3$. Any other components of the bottom layer should not lower the overall density of the bottom layer below 1 g/cm$^3$, preferably, not below about 1.1 g/cm$^3$. For example, the saccharide, sucrose, has a density of about 1.587 g/cm$^3$, and the electrolyte, sodium chloride, about 2.165 g/cm$^3$, so these would tend to make the bottom layer more dense, and give better separation between the bottom layer and the middle layer. However, the amount of water in the composition is crucial to the integrity of the composition. Water is less dense than the liquid polyols in the bottom layer, so adding water tends to make the density of the bottom layer more similar to the densities of the other two layers. Thus, adding too much water to the bottom layer reduces the rate at which the three layers separate after mixing, and the layers may also start to blend together and create aesthetically unappealing interfaces, if too much water is used. To avoid this, the amount of water in the bottom layer should be less than 10% by weight of the total composition, preferably less than 5%, and more preferably, less than about 2%. Conveniently, the amount of water can be used to fine tune the performance of the final composition Anhydrous compositions are also within the scope of this invention. Given that some incidental amounts of water may present in a compound ingredient, "anhydrous composition" means 0.001% or less of water, by weight of the composition.

Layer Interfaces

Now, for an acceptably thin interface (i.e. less than 0.5 mm) between the bottom and middle layers, it is preferable if the percent difference in densities is at least 3.0%, more preferably at least 5.0%, with the proviso that the density of the middle layer should be less than 0.98 g/cm$^3$. For example, if the bottom layer has a density of 1.02 g/cm$^3$, then the density of the middle layer, assuming a 5% difference, should be no more than 0.969 g/cm$^3$, but if the bottom layer has a density of about 1.1 g/cm$^3$, then the density of the middle layer should be no more than 0.98g/cm$^3$ (not 1.045 g/cm$^3$ that you would expect for a 5% difference). Liquid dimethicone, for example, has a density of about 0.965 g/cm$^3$.

In practice, achieving an acceptable interface between the bottom layer (with the liquid polyol phase) and the middle layer (with liquid silicone phase) is done first. Thereafter, an acceptably thin interface between the top layer (with liquid oil phase) and the middle layer depends heavily on the choice of base oil in the liquid oil phase. Suitable base oils may be found by trial and error, but we have mentioned some of the more useful base, oils above, especially jojoba oil.

Performance

One of the benefits of a three layered composition according to the present invention is that it can be mixed homogenously by manual shaking, and remain homogenous for a sufficient period of time to allow the consumer to use the product, before three distinct layers begin to re-form. A homogenous mixture is achieved in no more than 20 seconds by manual shaking, preferably no more than 10 seconds, more preferably no more than about 5 seconds. After shaking, the product remains homogenous (i.e. no distinct layers can be seen with the unaided eye) for 1 minute to 10 minutes, preferably for 1 minutes to 5 minutes, more preferably for about 2 minutes to about 5 minutes. After shaking, three distinct layers are visible the unaided eye in no more than 10 minutes, preferably no more than 5 minutes, more preferably no more than 2 minutes.

Auxiliary Ingredients

Any of the layers of the composition may comprise additional ingredients that provide a benefit to the composition or the user. The additional ingredients should not disturb the stability of the layer in which they are disbursed, and should not disturb the stability of the three phase configuration of the product. Ingredients that may be used include, but are not limited to fragrances, preservatives, dyes, emollients, buffers, hair care actives, skin care actives, thickeners, suspending agents, and various types of cosmetic or personal care ingredient.

Given the requirements of forming three layers of substantial size, that behave as described herein, the total concentration of all auxiliary ingredients in a composition according to the invention is limited to about 20% of the composition by weight, preferably no more than about 15% of the composition by weight, more preferably no more than about 10% of the composition by weight.

Of particular interest from a personal care point of view are sunscreen agents. One or more sunscreen agents should be compatible with the layer in which they are disbursed. Non-limiting examples of suitable oil-soluble sunscreens that may be dispersed in the top layer include benzophenone-3, bis-ethylhexyloxyphenol methoxyphenyl triazine, butyl methoxydibenzoyl-methane, diethylamino hydroxy-benzoyl hexyl benzoate, drometrizole trisiloxane, ethylhexyl methoxycinnamate, ethylhexyl salicylate, ethylhexyl triazone, octocrylene, homosalate, polysilicone-15, and derivatives and mixtures thereof. Non-limiting examples of suitable water-soluble sunscreens that may be dispersed in the bottom layer include phenylbenzimidazole sulfonic acid (PBSA), terephthalylidene dicamphor sulfonic acid, (Mexoryl™ SX), benzophenone-4, benzophenone-5, benzylidene camphor sulfonic acid, cinnamidopropyl-trimonium chloride, methoxycinnamido-propyl ethyldimonium chloride ether, disodium bisethylphenyl triaminotriazine stilbenedisulfonate, disodium distyrylbiphenyl disulfonate, disodium phenyl dibenzimidazole tetrasulfonate, methoxycinnamido-propyl hydroxysultaine, methoxycinnamido-propyl laurdimonium tosylate, PEG-25 PABA (p-aminobenzoic acid), polyquarternium-59, TEA-salicylate, derivatives and mixtures thereof. In certain embodiments, one or more sunscreens may comprise from about 0.001% to about 20% of the composition by weight, preferably about 0.001 to about 10% of the composition by weight, more preferably about 0.01 to about 5% of the composition by weight. Exact amounts will vary depending upon the chosen sunscreen agent and the desired Sun Protection Factor (SPF).

In addition, the formulation may be used for purposes other than hair care, and therefore the composition may include suitably useful active ingredients as well.

Furthermore, compositions of the present invention comprise less than 1% mineral oil, less that 1% salts, and non-substantial amounts of surfactant and emulsifier. It is also important that the composition does not comprises substantial amounts of fatty acids that might emulsify the phases and prevent them from separating or separating too slowly. "Substantial" amounts of surfactant, emulsifier, or fatty acid is an amount that would cause the total composition to fail in the performance parameters discussed above, especially those concerning the time for shaking, the time of remaining in a homogenous state, the time for distinct layers to reappear, and he thickness of the interfaces. Allowing that some amount of incidental surfactant, emulsifier or fatty acid may not cause product failure, a person of ordinary skill in the art could determine acceptable levels of these types of ingredients. Some of the most preferred compositions comprise no mineral oil, no salt, no surfactant, no emulsifier and no fatty acids.

The following is a non-limiting example of a stable three layered composition, having acceptably thin interfaces, and a clear, colorless middle layer, that can be made homogenous by manual shaking, that maintains homogeneity for at least one minute after shaking, and that forms three distinct layers within ten minutes after shaking.

| | Percent |
|---|---|
| BOTTOM LAYER (32.541%) | |
| glycerin | 6.00 |
| propanediol | 10.00 |
| butylene glycol | 12.00 |
| panthenyl ethyl ether | 0.50 |
| water/polyquaternium-55 | 0.001 |
| FD&C RED No. 40 (0.5% in BG) | 0.09 |
| saccharide isomerate | 1.00 |
| pantethine | 0.25 |
| panthenol | 0.25 |
| phytantriol | 0.25 |
| water | 1.50 |
| sodium chloride | 0.20 |
| sucrose | 0.50 |
| MIDDLE LAYER (41.50%) | |
| dimethicone (100 cs) | 37.00 |
| dimethicone* | 4.00 |
| dimethicone (100000 cs) | 0.50 |
| TOP LAYER (25.959%) | |
| jojoba oil | 22.199 |
| palm kernel oil | 0.05 |
| elaeis oleifera fruit oil | 0.10 |
| coconut oil | 0.30 |
| watermelon oil | 0.30 |
| ximenia Americana seed oil | 0.30 |
| kukui seed oil | 0.30 |
| sclerocarya birrea seed oil | 0.30 |
| jasmine flower wax | 0.20 |
| ethylhexyl methoxycinnamate | 0.10 |
| babassu oil | 0.30 |
| fragrance | 1.50 |
| commiphora wightii oil | 0.01 |

*Silicone HL-88 from Barnet Products Corp.

Each layer should be prepared separately, and subsequently mixed together. After mixing, the handling of the composition should be such that interfaces are allowed to develop between the top and middle layers and between the middle and bottom layers. Preferably, after mixing the three layers together, the composition is allowed to rest so that the interfaces may spontaneously form. For the consumer market, a final composition may be filled into a saleable size container (i.e. 15 mL-1000 mL). This must be done while the composition is still in a mixed, homogenous state, and thereafter, proper handling of the container will allow an interface to develop between the top and middle layers and between the middle and bottom layers. Alternatively, specific amounts of each layer could be poured into a container separately. Thereafter, proper handling of the container will allow the interfaces to develop. Of course, this alternative method requires three filling operations which is not advantageous.

With the choices of dye or other colorant for each of the layers, it is possible to manipulate the appearance of the finished composition to make a particular impression on the consumer. For example, in the composition of the example, red dye was added to the bottom layer. The middle layer is clear and colorless, and the top layer has a golden yellow color resulting naturally from the blend of oils. Because of the stunning visual appearance, saleable containers for the consumer market should be transparent, preferably colorless, glass bottles. In this way, the aesthetically pleasing and sophisticated appearance can be appreciated by the consumer.

Consumer Use

In use, a consumer shakes a closed container of composition vigorously enough to mix all three layers into a homogenous blend. In the compositions of the invention, the viscosity of the layers is such that a homogenous mixture is achievable in less than about 20 seconds of manual shaking While the composition is in a mixed, homogenous state, the consumer opens the container (i.e. removes a closure) and removes some of the mixed composition (i.e. she pours some of the composition into her hand or dips an applicator into the composition). Thereafter, the consumer applies the composition to her hair. Because the composition is homogenous, the three layers are dispensed in the same volume ratio that existed in the container. After use, the container is returned to a normal resting position. Within no more than 10 minutes, three distinct layers become visible in the composition that remains in the container.

In intended use, product is dispensed from the container when the product is in a homogenous state (i.e. after shaking) The ratio of the volumes of the three layers in the dispensed product is the same as in the original container, and the ratio of the volumes of the three layers in the container does not change over the life of the product. Thus, the consumer always gets the same application.

Packaging Considerations

The visual aesthetic effect made possible by the present invention may change as product in the container is used up. This is because as the residual product in the container decreases, the height of each layer changes. In general, they may not change by the same factor, it depends on the shape of the container in which the composition is disposed. If the container has an approximately constant cross section along the vertical direction, then the ratio of the heights of the three layers will not change, and the product will maintain a similar appearance throughout much of the life of the container.

Alternatively, if the container does not have a constant cross section along the vertical direction, then the ratio of the heights of the three layers will change. In this case, the product in the container will not maintain a similar appearance throughout the life of the container. For containers that have little or no symmetry, the change in appearance may be unpredictable. This change in the appearance of the consumer product may or may not be desirable.

A particularly pleasing effect is to have all three layers maintain the same height ratio throughout the life of the product. This is most easily achieved when over a substantial portion of its body, the container has a constant cross section (or nearly so) along the vertical direction. For example, a container might be approximately cylindrical, rectangular, or square between its base and its shoulder.

Furthermore, if the composition is filled into clear containers, and if each container is further packaged into an outer carton for the retail environment, then preferably, the outer carton allows the container to be seen. For example, the outer carton may have one or more windows. In one embodiment, the container is rectangular and the outer carton is rectangular. Two opposing faces of the carton have windows that expose the front and back of the container, and allow a consumer to look through the clear three layered product. The visual effect is significant.

The invention claimed is:

1. A cosmetic composition comprising by weight of the composition, 10-40% of a liquid top layer, 20-60% of a liquid middle layer, and 10-40% of a liquid bottom layer, wherein:
the top layer comprises at least 50% of one or more liquid base oils by weight of the top layer;
the middle layer comprises one or more liquid, linear silicones;
the bottom layer comprises at least 50% of one or more liquid polyols by weight of the bottom layer; and
the top and middle layers are separated by an interface and the middle and bottom layers are separated by an interface;
with the conditions that the composition comprises no more than 1% of salts and no more than 1% of mineral oil by weight of the composition.

2. The composition of claim 1 wherein the interfaces are less than 0.5 mm thick.

3. The composition of claim 2 wherein the interfaces are less than 0.25 mm thick.

4. The composition of claim 2 that comprises no surfactant, no emulsifier and no fatty acids.

5. The composition of claim 2 wherein the top layer comprises at least 50% jojoba oil by weight of the top layer and the bottom layer comprises at least 50% of diols and/or triols by weight of the bottom layer.

6. The composition of claim 5 wherein the diols include butylene glycol, and propanediol and the triols include glycerine.

7. The composition of claim 6 wherein the bottom layer further comprises sucrose and no more than 1% of sodium chloride by weight of the composition.

8. The composition of claim 5 wherein the middle layer comprises one or more clear, colorless, liquid, linear dimethicones having a viscosity of 100 cps to 100,000 cps.

9. The composition of claim 5 wherein the top layer further comprises palm kernel oil, elaeis oleifera fruit oil, coconut oil, watermelon seed oil, ximenia Americana seed oil, kukui seed oil, and sclerocarya birrea seed oil, and no mineral oil.

10. The composition of claim 1 wherein the amount of water in the bottom layer is less than 10% by weight of the total composition.

11. The composition of claim 1 that is anhydrous.

12. The composition of claim 1 further comprising one or more sunscreen agents from about 0.001% to about 20% of the composition by weight.

13. The composition of claim 2 wherein the percent difference in density of bottom layer to density of middle layer is at least 3%, and the density of the middle layer is less than 0.98 g/cm$^3$.

14. The composition of claim 1, characterized in that:
the three phases can be mixed by manual shaking, achieving homogeneity in no more than 20 seconds; and, after shaking has stopped:
remain homogenous for 1 to 10 minutes; and
reform three distinct layers in no more than about 10 minutes.

15. A method of making cosmetic composition for a consumer that comprises by weight of the composition, 10-40% of a liquid top layer, 20-60% of a liquid middle layer, and 10-40% of a liquid bottom layer, comprising the steps of:
preparing a top layer that comprises at least 50% of one or more liquid base oils by weight of the top layer;
preparing a middle layer that comprises one or more liquid, linear silicones; and
preparing a bottom layer that comprises at least 50% of one or more liquid polyols by weight of the bottom layer;
with the conditions that the composition comprises no more than 1% of salts and no more than 1% of mineral oil by weight of the composition;
mixing together the top, middle and bottom layers;
allowing an interface to develop between the top and middle layers and between the middle and bottom layers.

16. The method of claim 15 further comprising the step of filling the mixed composition into a saleable size container, before the step of allowing an interface to develop.

17. The method of claim 16 where in the saleable size container is transparent.

18. The method of claim 17 wherein the container is a colorless glass bottle that has a constant cross section along a vertical direction.

19. The method of claim 18 wherein the container has a base and shoulder and is cylindrical, rectangular, or square between the base and the shoulder.

20. The method of claim 17 further comprising the step of packaging the container into an outer carton, the outer carton having one or more windows that expose the container to a consumer.

* * * * *